United States Patent
Shieh et al.

(10) Patent No.: US 6,960,467 B2
(45) Date of Patent: Nov. 1, 2005

(54) BIOCHANNEL ASSAY FOR HYBRIDIZATION WITH BIOMATERIAL

(75) Inventors: Chan-Long Shieh, Paradise Valley, AZ (US); Barbara Foley, Phoenix, AZ (US); Huinan Yu, Chandler, AZ (US); Vi-En Choong, Chandler, AZ (US)

(73) Assignee: Clinical Micro Sensors, Inc., Pasadena, CA (US)

(*) Notice: Subject to any disclaimer, the term of this patent is extended or adjusted under 35 U.S.C. 154(b) by 656 days.

(21) Appl. No.: 10/028,277

(22) Filed: Dec. 19, 2001

(65) Prior Publication Data

US 2002/0094584 A1 Jul. 18, 2002

Related U.S. Application Data

(63) Continuation of application No. 09/438,600, filed on Nov. 12, 1999, now Pat. No. 6,361,958.

(51) Int. Cl.[7] ............................................. C12M 3/00
(52) U.S. Cl. ................. 435/287.2; 422/50; 422/68.1; 435/4; 435/6; 435/7.1; 435/287.1; 435/288.4; 435/288.5; 435/810; 436/514; 436/517; 436/518; 436/528
(58) Field of Search ................ 422/50, 68.1; 435/4, 435/6, 7.1, 287.1, 287.2, 288.4, 288.5, 810; 436/514, 517, 518, 528, 529, 531

(56) References Cited

U.S. PATENT DOCUMENTS

| | | |
|---|---|---|
| 4,415,732 A | 11/1983 | Caruthers et al. |
| 4,683,195 A | 7/1987 | Mullis et al. |
| 4,713,347 A | 12/1987 | Mitchell et al. |
| 4,755,458 A | 7/1988 | Rabbani et al. |
| 4,840,893 A | 6/1989 | Hill et al. |

(Continued)

FOREIGN PATENT DOCUMENTS

| | | |
|---|---|---|
| EP | 0 527 905 B1 | 8/1991 |
| EP | 0 637 998 B1 | 7/1996 |
| EP | 0 478 319 B1 | 4/1997 |
| EP | 0 637 996 B1 | 7/1997 |
| EP | 0 969 083 A1 | 1/2000 |
| EP | 1 183 102 B1 | 3/2002 |
| WO | WO 86/05815 A1 | 10/1986 |
| WO | WO 93/22053 A1 | 11/1993 |
| WO | WO 96/15576 A1 | 5/1996 |
| WO | WO 86/15450 A1 | 12/1996 |
| WO | WO 96/39260 A1 | 12/1996 |
| WO | WO 96/93252 A1 | 12/1996 |
| WO | WO 97/16561 A1 | 5/1997 |
| WO | WO 97/16835 A1 | 5/1997 |
| WO | WO 97/27324 A1 | 7/1997 |
| WO | WO 97/27329 A1 | 7/1997 |
| WO | WO 97/31256 A2 | 8/1997 |
| WO | WO 97/31256 A3 | 8/1997 |
| WO | WO 97/37755 A1 | 10/1997 |
| WO | WO 97/43629 A1 | 11/1997 |
| WO | WO 98/04740 A1 | 2/1998 |
| WO | WO 98/05424 A1 | 2/1998 |
| WO | WO 98/12539 A1 | 3/1998 |
| WO | WO 98/43739 | 3/1998 |
| WO | WO 98/13683 A1 | 4/1998 |
| WO | WO 98/32018 A1 | 7/1998 |
| WO | WO 98/49344 A1 | 11/1998 |

(Continued)

*Primary Examiner*—Christopher L. Chin
(74) *Attorney, Agent, or Firm*—Dorsey & Whitney LLP; Robin M. Silva

(57) ABSTRACT

The invention relates to a microfluidic device with microchannels that have separated regions which have a member of a specific binding pair member such as DNA or RNA bound to porous polymer, beads or structures fabricated into the microchannel. The microchannels of the invention are fabricated from plastic and are operatively associated with a fluid propelling component and detector.

24 Claims, 3 Drawing Sheets

U.S. PATENT DOCUMENTS

| | | |
|---|---|---|
| 4,920,047 A | 4/1990 | Giaever et al. |
| 5,015,569 A | 5/1991 | Pontius |
| 5,064,618 A | 11/1991 | Baker et al. |
| 5,066,372 A | 11/1991 | Weetall |
| 5,071,531 A | 12/1991 | Soane |
| 5,126,022 A | 6/1992 | Soane et al. |
| 5,130,238 A | 7/1992 | Malek et al. |
| 5,135,627 A | 8/1992 | Soane |
| 5,147,607 A | 9/1992 | Mochida |
| 5,192,507 A | 3/1993 | Taylor et al. |
| 5,296,375 A | 3/1994 | Kricka et al. |
| 5,304,487 A | 4/1994 | Wilding et al. |
| 5,455,166 A | 10/1995 | Walker |
| 5,486,335 A | 1/1996 | Wilding et al. |
| 5,494,810 A | 2/1996 | Barany et al. |
| 5,498,392 A | 3/1996 | Wilding et al. |
| 5,505,321 A | 4/1996 | Caron et al. |
| 5,519,635 A | 5/1996 | Miyake et al. |
| 5,552,270 A | 9/1996 | Khrapko et al. |
| 5,569,364 A | 10/1996 | Hooper et al. |
| 5,585,069 A | 12/1996 | Zanzucchi et al. |
| 5,587,128 A | 12/1996 | Wilding et al. |
| 5,591,578 A | 1/1997 | Meade et al. |
| 5,593,838 A | 1/1997 | Zanzucchi et al. |
| 5,595,908 A | 1/1997 | Fawcett et al. |
| 5,603,351 A | 2/1997 | Cherukuri et al. |
| 5,605,662 A | 2/1997 | Heller et al. |
| 5,620,850 A | 4/1997 | Bamdad et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,643,738 A | 7/1997 | Zanzucchi et al. |
| 5,653,939 A | 8/1997 | Hollis et al. |
| 5,681,484 A | 10/1997 | Zanzucchi et al. |
| 5,694,932 A | 12/1997 | Michel |
| 5,705,346 A | 1/1998 | Okamoto et al. |
| 5,705,348 A | 1/1998 | Meade et al. |
| 5,716,825 A | 2/1998 | Hancock et al. |
| 5,726,026 A | 3/1998 | Wilding et al. |
| 5,727,548 A | 3/1998 | Hill et al. |
| 5,728,532 A | 3/1998 | Ackley |
| 5,741,462 A | 4/1998 | Nova et al. |
| 5,747,169 A | 5/1998 | Fan et al. |
| 5,750,015 A | 5/1998 | Soane et al. |
| 5,755,942 A | 5/1998 | Zanzucchi et al. |
| 5,756,050 A | 5/1998 | Ershow et al. |
| 5,759,866 A | 6/1998 | Machida et al. |
| 5,770,029 A | 6/1998 | Nelson et al. |
| 5,770,369 A | 6/1998 | Meade et al. |
| 5,780,235 A | 7/1998 | Bandman et al. |
| 5,824,473 A | 10/1998 | Meade et al. |
| 5,837,859 A | 11/1998 | Teoule et al. |
| 5,843,767 A | 12/1998 | Beattie |
| 5,849,486 A | 12/1998 | Heller et al. |
| 5,863,502 A | 1/1999 | Southgate et al. |
| 5,866,345 A | 2/1999 | Wilding et al. |
| 5,942,443 A | 8/1999 | Parce et al. |
| 5,952,172 A | 9/1999 | Meade et al. |
| 5,976,802 A | 11/1999 | Ansorge et al. |
| 6,013,170 A | 1/2000 | Meade |
| 6,013,459 A | 1/2000 | Meade |
| 6,063,573 A | 5/2000 | Kayyem |
| 6,063,589 A | 5/2000 | Kellogg et al. |
| 6,071,699 A | 6/2000 | Meade et al. |
| 6,087,100 A | 7/2000 | Meade et al. |
| 6,090,933 A | 7/2000 | Kayyem et al. |
| 6,096,825 A | 8/2000 | Garnier |
| 6,100,045 A | 8/2000 | Van Es |
| 6,100,099 A | 8/2000 | Gordon et al. |
| 6,114,122 A | 9/2000 | Besemer et al. |
| 6,150,119 A | 11/2000 | Kopf-Sill et al. |
| 6,150,180 A | 11/2000 | Parce et al. |
| 6,177,250 B1 | 1/2001 | Meade et al. |
| 6,180,352 B1 | 1/2001 | Meade et al. |
| 6,197,515 B1 | 3/2001 | Bamdad et al. |
| 6,197,595 B1 | 3/2001 | Anderson et al. |
| 6,200,761 B1 | 3/2001 | Meade et al. |
| 6,203,758 B1 | 3/2001 | Marks et al. |
| 6,207,369 B1 | 3/2001 | Wohlstadter et al. |
| 6,221,583 B1 | 4/2001 | Kayyem et al. |
| 6,221,677 B1 | 4/2001 | Wu et al. |
| 6,232,062 B1 | 5/2001 | Kayyem et al. |
| 6,238,870 B1 | 5/2001 | Meade et al. |
| 6,258,545 B1 | 7/2001 | Meade et al. |
| 6,258,593 B1 | 7/2001 | Schembri et al. |
| 6,264,825 B1 | 7/2001 | Blackburn et al. |
| 6,265,155 B1 | 7/2001 | Meade et al. |
| 6,268,149 B1 | 7/2001 | Meade et al. |
| 6,268,150 B1 | 7/2001 | Meade et al. |
| 6,277,576 B1 | 8/2001 | Meade et al. |
| 6,290,839 B1 | 9/2001 | Kayyem et al. |
| 6,291,188 B1 | 9/2001 | Meade et al. |
| 6,300,141 B1 | 10/2001 | Segal et al. |
| 6,306,584 B1 | 10/2001 | Bamdad |
| 6,306,590 B1 | 10/2001 | Mehta et al. |
| 6,322,979 B1 | 11/2001 | Bamdad et al. |
| 6,326,211 B1 | 12/2001 | Anderson et al. |
| 6,361,958 B1 * | 3/2002 | Shieh et al. ............... 435/7.1 |
| 6,368,871 B1 | 4/2002 | Christel et al. |
| 6,432,723 B1 | 8/2002 | Plaxco et al. |
| 6,472,148 B1 | 10/2002 | Bamdad et al. |
| 6,479,240 B1 | 11/2002 | Kayyem et al. |
| 6,495,323 B1 | 12/2002 | Kayyem et al. |
| 6,541,617 B1 | 4/2003 | Bamdad et al. |
| 6,572,830 B1 | 6/2003 | Burdon et al. |
| 6,592,696 B1 | 7/2003 | Burdon et al. |
| 6,600,026 B1 | 7/2003 | Yu |
| 6,623,945 B1 | 9/2003 | Nair et al. |
| 2002/0006643 A1 | 1/2002 | Kayyem et al. |
| 2002/0009810 A1 | 1/2002 | O'Connor et al. |
| 2002/0177135 A1 | 11/2002 | Doung et al. |
| 2003/0087228 A1 | 5/2003 | Bamdad et al. |

FOREIGN PATENT DOCUMENTS

| | | |
|---|---|---|
| WO | WO 98/51823 A1 | 11/1998 |
| WO | WO 99/29711 A1 | 6/1999 |
| WO | WO 99/33559 A1 | 7/1999 |
| WO | WO 99/37819 A2 | 7/1999 |
| WO | WO 99/37819 A3 | 7/1999 |
| WO | WO 99/67425 A3 | 12/1999 |
| WO | WO 99/67425 A2 | 12/1999 |
| WO | WO 00/62931 A1 | 10/2000 |
| WO | WO 01/06016 A3 | 1/2001 |
| WO | WO 01/06016 A2 | 1/2001 |
| WO | WO 01/35100 A2 | 5/2001 |
| WO | WO 01/54813 A3 | 8/2001 |
| WO | WO 01/54813 A2 | 8/2001 |
| WO | WO 02/43864 A2 | 6/2002 |

\* cited by examiner

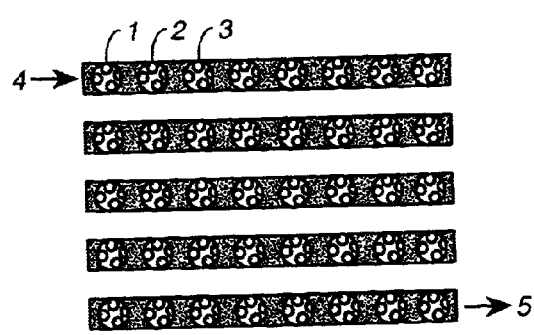
FIG._1
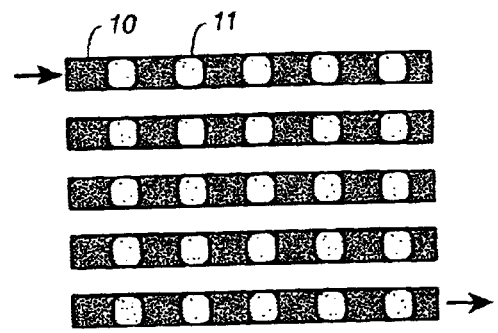
FIG._2
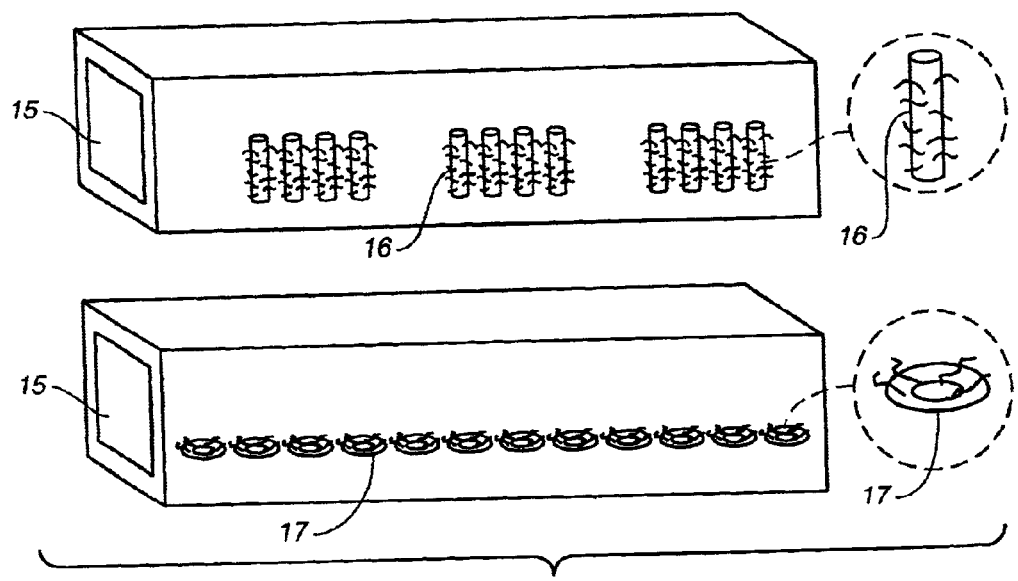
FIG._3

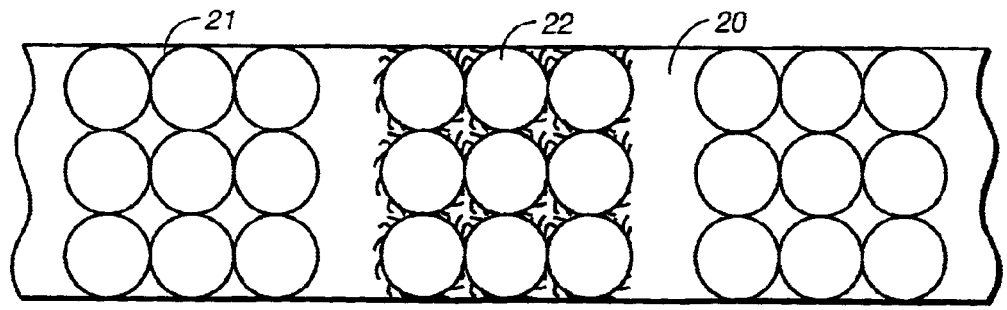
FIG._4
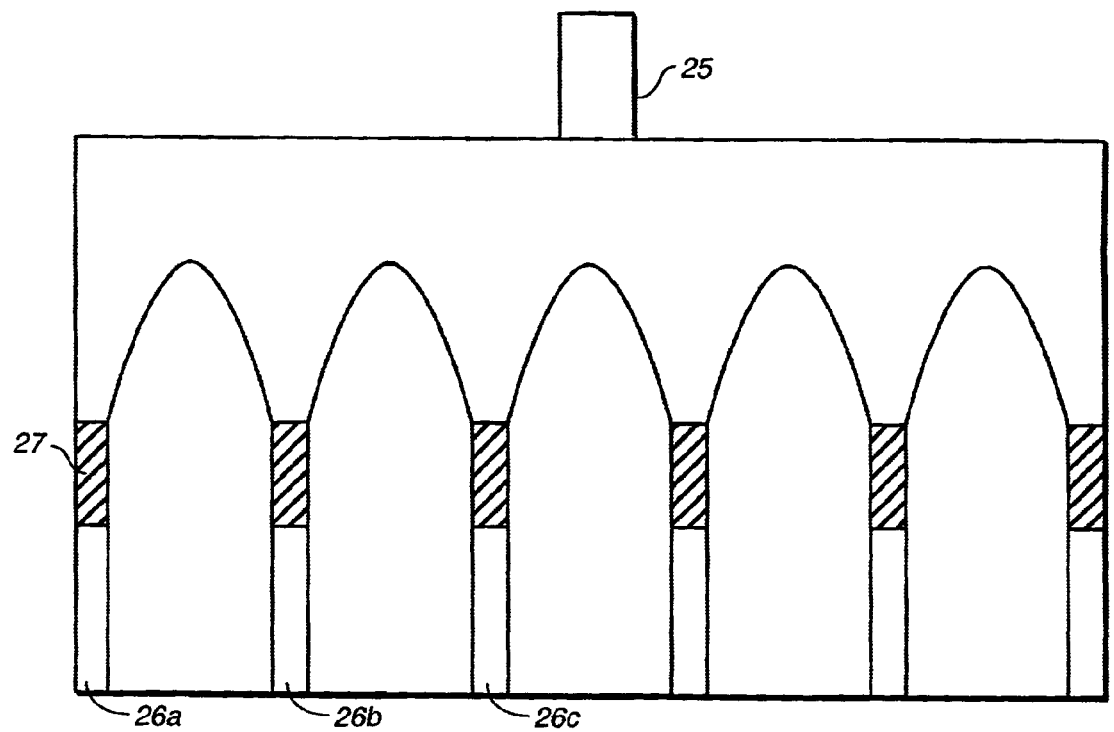
FIG._5

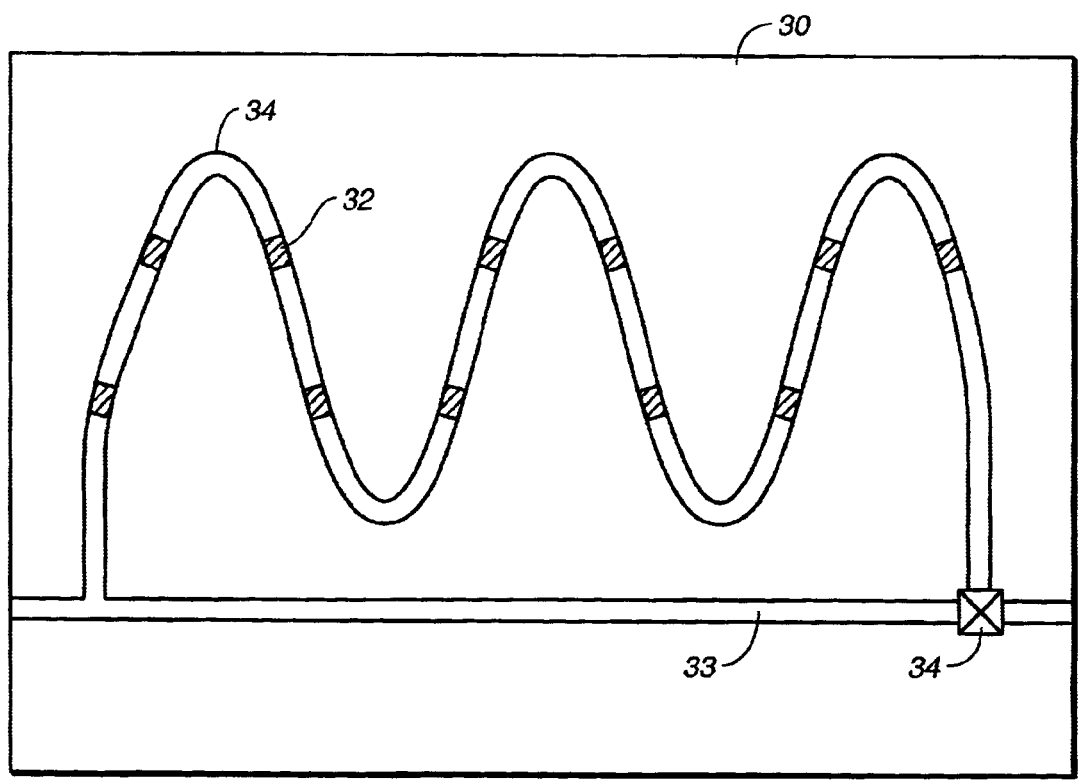
FIG._6

BIOCHANNEL ASSAY FOR HYBRIDIZATION WITH BIOMATERIAL

This application is, a continuation of U.S. Ser. No. 09/438,600, filed Nov. 12, 1999, now U.S. Patent No. 6,361,958, issued Mar. 26, 2002, and is hereby incorporated by reference in its entirety.

BACKGROUND OF THE INVENTION

1. Field of the Invention

The invention pertains to the structure, fabrication of a microfluidic device and methods for conducting analysis in microfluidic devices.

2. Background of the Art Related to the Invention

Analysis utilizing specific binding pairs such as antigen/antibody; complementary DNA/DNA; DNA/RNA; RNA/RNA; biotin/avidin containing pairs are widely known in the art. Techniques for manufacturing and utilizing microfluidic devices are also well known. The art also discloses various techniques for DNA sequencing based on complementary binding of DNA.

DNA probe array technology, which utilizes binding of target single standed DNA onto immobilized DNA probes has wide applications. A large amount of research and development activities have been carried out with different technology emphasis. For example, same technologies are focused on probe placement by mechanical means. Other technologies are focused on in-situ probe synthesis that is advantageous in producing large arrays. Additionally, other technologies are focused on gel pad arrays using photopolymerizaion and piezoelectric liquid dispensing technologies.

A common challenge to all DNA hybridization technologies is the lack of control of stringency for each individual probe site. The DNA hybridization process occurs at specific temperature and salinity conditions and varies with DNA sequences. For DNA probe arrays, since the DNA probe sequences are different, hybridization recognition is never perfect under a uniform stringency condition for the entire probe array. The problem is most obvious for short duplexes which often results in single base mismatches. One can minimize the effect of mismatched hybridization by using large probe site redundancy. Stringency control has been provided for each probe site by controlling the electrophoretic movement of oligonucleotides. To successfully implement this later scheme, a meticulously engineered permeation layer is required to prevent DNA molecules or labeling agents being damaged by direct electrolysis or by the product of the electolysis.

In addition, the current DNA array technologies have failed to provide an effective solution to maximize hybridization efficiency. For diagnostic assays, the target DNA molecules are often of minute quantities. The detection limit of the assay is determined by the sensitivity of the detection device, and also by the amount of target oligos bound to the probes during the course of hybridization. In a stationary hybridization chamber where active mixing is absent, the probability of a given target molecule hybridizes to its complementary strand on the surface is determined by diffusion rate and statistics. It takes up to tens of hours for hybridization to complete at low target concentration levels. To better utilize the target molecules and enhance the hybridization, flow through technology has been proposed where the probe arrays are placed perpendicular to the fluidic flow direction. Even with flow through technology, only a portion of the target molecules can come in contact with any specific DNA probe site.

The present invention overcomes the above technical issues by sequentially placing the DNA probe sites in microfluidic channels such that the DNA probe can efficiently contact its binding partner.

U.S. Pat. No. 5,147,607 describes a variety of microassay devices which have microchannels in plastic materials with a reagent such as an antibody or DNA immobilized on the channel at different locations. Techniques for binding antibodies to the microchannel wall are described but techniques for binding DNA are not described. The binding of probes to the microchannel wall does not provide for optimum contact of probe and test sample. U.S. Pat. No. 5,843,767 describes microfabricated flowthrough porous apparatus for discrete detection of binding reactions such as DNA/DNA. WO/98/43739 describes porous flow channels having reagents immobilized in the chamber.

BRIEF DESCRIPTION OF THE DRAWINGS

FIG. 1 shows a schematic top view of a fluid channel filled with porous gel and spotted DNA probes.

FIG. 2 shows lithographically patterned gel pads inside a microfluidic channel.

FIG. 3 shows microfluidic channels with molded plastic microstructures for DNA attachment.

FIG. 4 shows a microfluidic channel packed with beads where distinct sections of beads have a specific binding agent such as DNA.

FIG. 5 illustrates a simple initial flow being directed into numerous channels.

FIG. 6 illustrates a circulating microfluidic channel device.

SUMMARY OF THE INVENTION

The invention comprises microfluidic devices comprising a section of solid material such as a chip with a microchannel with an inlet and exit port for flowing fluids through the channels. The microchannel has separated defined regions of specific binding pair member immobilized on porous polymer, microstructures molded in the microchannels or packed beads. These structures provide for optimum contact of the immobilized binding pair member and a binding pair member in fluid flowing through the mirochannel. The porous polymer beads or microstructure must provide for flow and not obstruct the channel. The microchannel is operatively associated with a detector and a fluid propeling component to flow liquids in the channel and may also have electrodes at the exit and entrance ports.

DNA/DNA; DNA/RNA, and RNA/RNA complementary binding pair are preferred. The microchannel is operatively associated with target DNA labeled with a fluorophore, an excitation source and a detector to detect emitted fluorescence from the binding pairs. It is an object of the invention to provide a method for DNA or RNA sequencing by providing the above identified chip with DNA or RNA probes immobilized in the separated defined region to bind fluorescently labeled target DNA.

It is also an object of the present invention to provide a means determining genetic defects. The invention also provides a means for identifying pathogens through DNA analysis.

The microchannels may have a variety of configurations, feedback arms, valves, and vents to control fluid flow. There may be single or multiple channels. The invention provides for efficient contact between immobilized binding substances and binding partners in the fluid flowing through the channel. The invention provides for improved hybridization stringency control by flow modulation; shortened assay time by increasing the rate of hybridization with flow induced agitation and by bringing the target and probe into proximity within the microfluidic channel; and increased hybridization efficiency which improves sensitivity. In addition there is no interference through hydrolysis.

DETAILED DESCRIPTION OF THE INVENTION

The chips microfluidic channels of the present invention are channels generally less than 200 microns in plastic with molding or embossing technology. The channels need to be of the dimension to support pumping of the microfluidic system The microfluidic channel may have any shape, for example, it may be linear, serpentine, arc shaped and the like. The cross-sectional dimension of the channel may be square, rectagular, semicircular, etc. There may be multiple and interconnected microchannels with valves to provide for recirculation.

The section of solid material maybe chips made of glass, ceramic, metal, silicon or plastic. Chips are preferably fabricated from plastics such as expoxy resin, polyacrylic resins, polyester resins, polystyrene, polycarbonate, polyvinyl chloride and the like. Specific binding pairs are DNA/DNA or DNA/RNA complementary binding pairs.

Fluid propelling components such as pressurized gas, vacuum, electric field, magnetic field and cetrifugal force devices are operatively associated with the microchannel to move fluid through the microchannel. In addition, charged test samples may be altered by modulating the electric field against or in the direction of the flow or perpendicular to the flow. Thus, the rate of fluid flow in the microchannel can be altered to promote binding of binding pairs, for example, hybridization of DNA/DNA or DNA/RNA pairs. Also, operatively associated with the microchannel is a detector such as an optical, electrical or electrochemical detector.

FIG. 1 illustrates a serpentine shaped microfluidic channel 1 filled with porous gel 2 with discrete separate regions 3 which have attached a member of a specific binding pair, such as DNA. Sample flows into the microfluidic channel 4 and exits the channel at 5. In this approach, the channel is filled with porous gel material such as agarose or polyacrylamide. The pores of the gel are made large enough by using dilute gelling solutions to permit significant fluid flow through the gel members of specific binding pair is spotted onto the gels so that the probes are chemically attached.

FIG. 2 illustrates a microfluidic channel 10 which has patterned gel pads 11 within the channel. The gel pads are formed by photopolymerization of acrylamide using lithographic techniques.

FIG. 3 illustrates a microfluidic channel 15 where high surface area microstructures are molded into the channel. FIG. 3a shows a series of columns 16 in a distinct region and FIG. 3b shows a distinct region of doe 17 molded into channel 15 These microstructures are chemically modified and specific binding substances are attached.

FIG. 4 illustrates a microfluidic channel 20 packed alternately with regions of plain beads 21 and beads 22 having a specific binding substance, such as DNA.

FIG. 5 illustrates a microfluidic channel 25 which branches in multiple microfluidic channels 26a, b, c etc.; each of which have a distinct region of a binding substance 27 as described above. Through this embodiment, a sample can be studied in parallel to test its reactivity to the same or different specific binding substance.

FIG. 6 illustrates a chip 30 with a recirculating microfluidic channel 34. The microfluidic channel has discrete areas with specific binding substances 32 as described above and a recirculating arm 33 and a valve 34 for output after recirculation. In this embodiment the test sample is recirculated past the location of the binding partner. Thus, dilute samples or slow reacting samples can be respectively passed by the specific binding substance.

Microfabricated plastic capillary electrophoresis (CE) devices have been demonstrated in the art. Thermoplastic molded polymethylmethacrylate CE devices are described by R. M. McCormick, et al, "Microchannel electrophoretic separations of DNA in injection-molded plastic substrates," *Anal. Chem.*, vol. 69, pp. 2626, 1997. Eckstrom et al. investigated elastomeric polymers such as PDMS, "PCT Appl. WO91/16966, " 1991. More recently, others have published electrophoretic separation of DNA ladders in PDMS devices, for example, C. S. Effenhauser, et al, "Integrated Capillary Electrophoresis on Flexible Silicone Microdevices," *Anal Chem.*, vol. 69, pp. 3451, 1997. Mastrangelo, et al describes building micro CE devices based on parylene-polycarbonate substrates using a surface micromachining approach, "An Inexpensive Plastic Technology for Microfabricated Capillary Electroophoresis Chip" presented at Micro-TAS'98, Banff, 1998.Thus, techniques are available for fabricating microchannels. The invention involves fixing specific binding substances by way of porous polymer, beads or structure in the microchannel to more efficiently promote binding.

These examples are intended to illustrate the present invention and not to limit it in spirit or scope.

What is claimed:

1. A microfluidic device comprising:
   (i) a first microchannel comprising a plurality of spatially distinct regions upon which a member of a specific binding pair is immobilized;
   (ii) at least a first entrance port and at least a first exit port for the transportation of at least one test sample;
   (iii) a fluid propelling component that controls that flow rate of said test sample; and
   (iv) a recirculating arm for recirculating said test sample across a spatially distinct regions.

2. A microfluidic device according to claim 1, wherein said first microchannel is serpentine.

3. A microfluidic device according to claim 1, further comprising at least one valve in said exit port.

4. A microfluidic device according to claim 1, wherein said first microchannel branches into multiple second microfluidic channels each of which comprises a plurality of spatially distinct regions upon which a member of a specific binding pair is immobilized.

5. A microfluidic device according to claim 1 or 4, wherein said device is fabricated from a material selected from the group consisting of silicon, silicon dioxide, glass, plastic and ceramic.

6. A microfluidic device according to claim 1, where in said spatially distinct regions comprise porous polymers.

7. A microfluidic device according to claim 6, wherein said porous polymer is a a hydrogel pad.

8. A microfluidic device according to claim 7, wherein said hydrogel pad is a patterned gel pad further comprising spatially separated portions within said hydrogel pad.

9. A microfluidic device according to claim 1, wherein each of said spatially distinct regions has a different member of a specific binding pair immobilized thereto.

10. A microfluidic device according to claim 1, wherein said spatially distinct regions in said microchannel comprise beads with said member of said specific binding pair immobilized thereto.

11. A microfluidic device according to claim 1, wherein said spatially distinct regions comprise microstructures fabricated into said microchannel.

12. A microfluidic device according to claim 1, wherein said microstructures comprise a series of columns molded into said first microchannel.

13. A microfluidic device according to claim 1, wherein said microstructures comprise domes molded into said first microchannel.

14. A microfluidic device according to claim 1, wherein said specific binding pair members are nucleic acids.

15. A microfluidic device according to claim 14, wherein said nucleic acid is a DNA.

16. A microfluidic device according to claim 14, wherein said nucleic acid is a RNA.

17. A microfluidic device according to claim 1, wherein said specific binding pair members are proteins.

18. A microfluidic device according to claim 17, wherein the proteins for one member of said specific binding pair are antigens.

19. A microfluidic device according to claim 17, wherein the proteins for one member of said specific binding pair are antibodies.

20. A microfluidic device according to claim 1, wherein said fluid propelling component comprises a pressurized gas, a vacuum, an electrical field, a magnetic field or a centrifugal force.

21. A method of detecting a specific binding member in a test sample, said method comprising passing said test sample through the microfluidic device described in claim 1, 2, or 4, to form a binding pair and detecting said binding pair.

22. A method according to claim 21, wherein said test sample is recirculated.

23. A method according to claim 21, wherein the flow rate of said test sample is adjusted using a fluid propelling component to increase contact between said binding pairs.

24. A method according to claim 21, wherein said fluid propelling component comprises a pressurized gas, a vacuum, an electrical field, a magnetic field or a centrifugal force.

* * * * *